(12) United States Patent
Kennedy et al.

(10) Patent No.: US 10,575,750 B2
(45) Date of Patent: Mar. 3, 2020

(54) NEUROTROPHIC ELECTRODE SYSTEM

(71) Applicants: Philip Kennedy, Duluth, GA (US); Maysam Ghovanloo, Atlanta, GA (US)

(72) Inventors: Philip Kennedy, Duluth, GA (US); Maysam Ghovanloo, Atlanta, GA (US)

(73) Assignee: Neural Signals, Inc., Duluth, GA (US)

( * ) Notice: Subject to any disclaimer, the term of this patent is extended or adjusted under 35 U.S.C. 154(b) by 589 days.

(21) Appl. No.: 15/380,097

(22) Filed: Dec. 15, 2016

(65) Prior Publication Data

US 2017/0164863 A1  Jun. 15, 2017

Related U.S. Application Data

(60) Provisional application No. 62/267,366, filed on Dec. 15, 2015.

(51) Int. Cl.
*A61B 5/00* (2006.01)
*A61B 5/0478* (2006.01)
*H02J 50/12* (2016.01)

(52) U.S. Cl.
CPC .......... *A61B 5/0478* (2013.01); *A61B 5/0006* (2013.01); *H02J 50/12* (2016.02); *A61B 5/6868* (2013.01); *A61B 2560/0214* (2013.01)

(58) Field of Classification Search
CPC . A61B 5/0478; A61B 5/04001; A61B 5/0006; A61B 5/6846; A61B 5/6867; A61B 2562/0209; A61B 2562/125; A61B 2560/0214; H02J 50/12
See application file for complete search history.

(56) References Cited

U.S. PATENT DOCUMENTS

| | | | |
|---|---|---|---|
| 4,852,573 A * | 8/1989 | Kennedy | A61B 5/0006 600/377 |
| 2006/0282014 A1* | 12/2006 | Kipke | A61B 5/04001 600/573 |
| 2013/0144145 A1* | 6/2013 | Meng | A61B 5/04001 600/377 |
| 2014/0094674 A1* | 4/2014 | Nurmikko | A61B 5/04001 600/378 |
| 2014/0200681 A1* | 7/2014 | Kennedy | A61B 5/0006 623/25 |

OTHER PUBLICATIONS

Yeon et al., "Optimal design of a 3-coil inductive link for millimeter-sized biomedical implants" Oct. 17, 2016, IEEE, Shanghai, China.

* cited by examiner

*Primary Examiner* — Eun Hwa Kim
*Assistant Examiner* — Rachel A. Vierra
(74) *Attorney, Agent, or Firm* — Bryan W. Bockhop; Bockhop Intellectual Property Law, LLC

(57) ABSTRACT

A neurotrophic electrode system includes a non-conductive cone, a multi-channel electrode assembly, a dielectric ribbon and a neurite-attracting substance disposed within the cone. The non-conductive cone consists essentially of a material that is stable in a neural environment and defines a cavity. The cavity opens to a small opening at a first end of the cone and opens to a large opening at a second end of the cone that is opposite the first end. The multi-channel electrode assembly includes at least two recording sites that are disposed within the cavity defined by the cone. Each recording site is coupled to a wire that extends out of the large end of the cone. Each wire ends in a connection pad. The dielectric ribbon encases all of the wires but exposes each recording site and exposes each connection pad.

19 Claims, 4 Drawing Sheets

NEUROTROPHIC ELECTRODE SYSTEM

CROSS-REFERENCE TO RELATED APPLICATION(S)

This application claims the benefit of U.S. Provisional Patent Application Ser. No. 62/267,366, filed Dec. 15, 2015, the entirety of which is hereby incorporated herein by reference.

BACKGROUND OF THE INVENTION

1. Field of the Invention

The present invention relates to neural electrodes and, more specifically, to a neurotrophic electrode system.

2. Description of the Related Art

Neural electrodes are designed to be implanted into the brains of patients to detect neural potentials generated as a result of neural activity. Such electrodes can be used to allow locked in individuals to control devices through a computer interface. In one use, neural electrodes have been used to generate phonemes as part of speech synthesis.

Neurotrophic electrodes are neural electrodes that include a neurotrophic factor that stimulates the growth of neurites into the neural electrode. One type neurotrophic electrode assembly includes one or more wires that extend into a glass cone. Neurites grown into the cone and an exposed portion of the wire (referred to as a "recording site") collects data from the neurites. These electrode assemblies tend to be limited to having only one or two wires due to the bulkiness of the wires.

Advanced neural interface applications require multiple recording sites to enable collection of sufficient data for the application. As typical electrodes are limited to having only one or two recording sites, several different implants are necessary for such advanced applications.

Therefore, there is a need for a neurotrophic electrode system that includes multiple recording sites in a single assembly.

SUMMARY OF THE INVENTION

The disadvantages of the prior art are overcome by the present invention which, in one aspect, is a neurotrophic electrode system that includes a non-conductive cone, a multi-channel electrode assembly, a dielectric ribbon and a neurite-attracting substance disposed within the cone. The non-conductive cone consists essentially of a material that is stable in a neural environment and defines a cavity. The cavity opens to a small opening at a first end of the cone and opens to a large opening at a second end of the cone that is opposite the first end. The multi-channel electrode assembly includes at least two recording sites that are disposed within the cavity defined by the cone. Each recording site is coupled to a wire that extends out of the large end of the cone. Each wire ends in a connection pad. The dielectric ribbon encases all of the wires but exposes each recording site and exposes each connection pad.

In another aspect, the invention is a neural electrode system that includes a non-conductive cone, a multi-channel electrode assembly, a dielectric ribbon and a neurite-attracting substance disposed within the cone. The non-conductive cone consists essentially of a material that is stable in a neural environment and defines a cavity. The cavity opens to a small opening at a first end of the cone and opens to a large opening at a second end of the cone that is opposite the first end. The non-conductive cone defines at least one side opening in communication with the cavity in which the side opening is disposed between the large opening and the small opening. The multi-channel electrode assembly includes at least two recording sites that are disposed within the cavity defined by the cone. Each recording site is coupled to a wire that extends out of the large end of the cone. Each wire ends in a connection pad. The dielectric ribbon encases all of the wires but exposes each recording site and exposes each connection pad.

In yet another aspect, the invention is a method of making a neurotrophic electrode system, in which a non-conductive cone that defines a cavity that opens to a narrow first end and to a wide second end opposite the first end is formed. A multi-channel electrode assembly is partially encased in a dielectric ribbon. The multi-channel electrode assembly includes at least two recording sites that are exposed and a wire extending from each of the recording sites. Each wire ends in a connection pad. The multi-channel electrode assembly is placed into the cavity through the second end so that the recording sites are disposed adjacent to the first end.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

Figure 1:
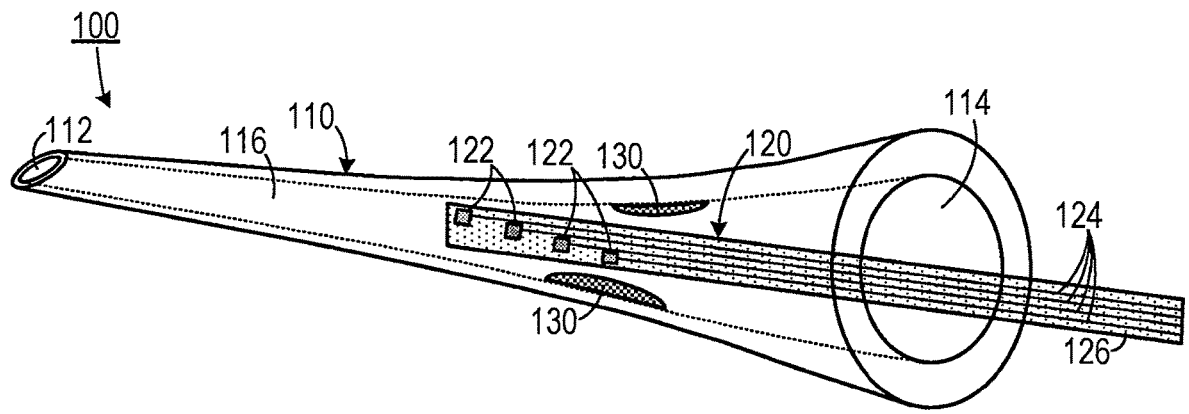
FIG. 1 is a perspective view of one embodiment of a neurotrophic electrode system.

A preferred embodiment of the invention is now described in detail. Referring to the drawings, like numbers indicate like parts throughout the views. Unless otherwise specifically indicated in the disclosure that follows, the drawings are not necessarily drawn to scale. As used in the description herein and throughout the claims, the following terms take the meanings explicitly associated herein, unless the context clearly dictates otherwise: the meaning of "a," "an," and "the" includes plural reference, the meaning of "in" includes "in" and "on."

U.S. Pat. No. 4,852,573, issued to Kennedy, is incorporated herein by reference for the purpose of disclosing methods of making and using implantable neural electrodes. U.S. Patent Publication No. 2009/0015075 A1, filed by Cook et al., is incorporated herein by reference for the purpose of disclosing wireless energy transfer systems.

As shown in FIG. 1, one embodiment of a neurotrophic electrode 100 includes a cone 110 with an open small end 112 and an opposite open large end 114, which defines a cavity 116 therein. A multi-channel electrode assembly 120 is affixed to the cone 110 inside the cavity 116. The multi-channel electrode assembly 120 includes a plurality of exposed recording sites 122 that are each coupled to a different wire 124. In one embodiment, the recording sites 122 would be on the order of 10μ×10μ 20μ×20μ. The wires 124 are encased in a dielectric ribbon 126 (such as a polyamide, polytetrafluoroethylene—which is sold under the mark Teflon®, or apoly(p-xylylene) polymer which sold under the mark Parylene®, etc., film) and extend outside of the cone 110 through the open large end 114. Once implanted, neurons will grow into the cavity 116 through the opening in the small end 112, thereby securing the neurotrophic electrode 100.

The cone 110 can be made of such materials as glass, silicon, quartz, polyamide or one of many non-conducting materials that are stable in a neural environment. Typically, the wires 124 would be made of a non-corroding conductor such as platinum or gold. While the diagram shows only four wires/recordation sites, many more wire/recordation sites may be used. Using a large number of wire/recordation sites allows for the sensing of more complex neural potential patterns.

Prior to implantation, a material 130 that attracts neurites into the cone 110 is placed therein. Examples of such a material 130 include neural growth factors, nerve segments, endothelium, stem cells, and combinations thereof.

If stem cells are used, one method of acquiring such stem cells would be to take autologous stem cells a fat layer in the patient, which could be harvested subcutaneously one or two days before surgery using known methods. The stem cells would then be injected into the cone 110 shortly before implantation.

Figure 2:
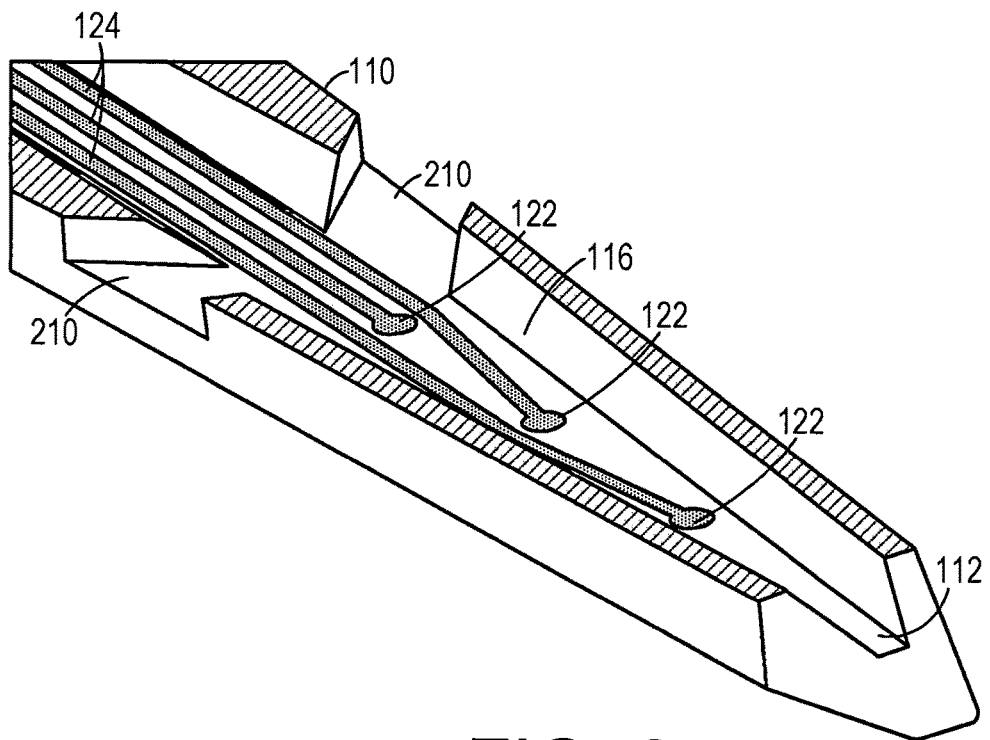
FIG. 2 is a cut-away view of a second embodiment of a neurotrophic electrode system in which side openings are defined in a cone.

As shown in FIG. 2, in one embodiment can include side openings 210 to the cavity 116. Such openings 210 provide additional passages into which neurites can grow and also further secure the electrode in the neural tissue into which it is implanted.

Figure 3:
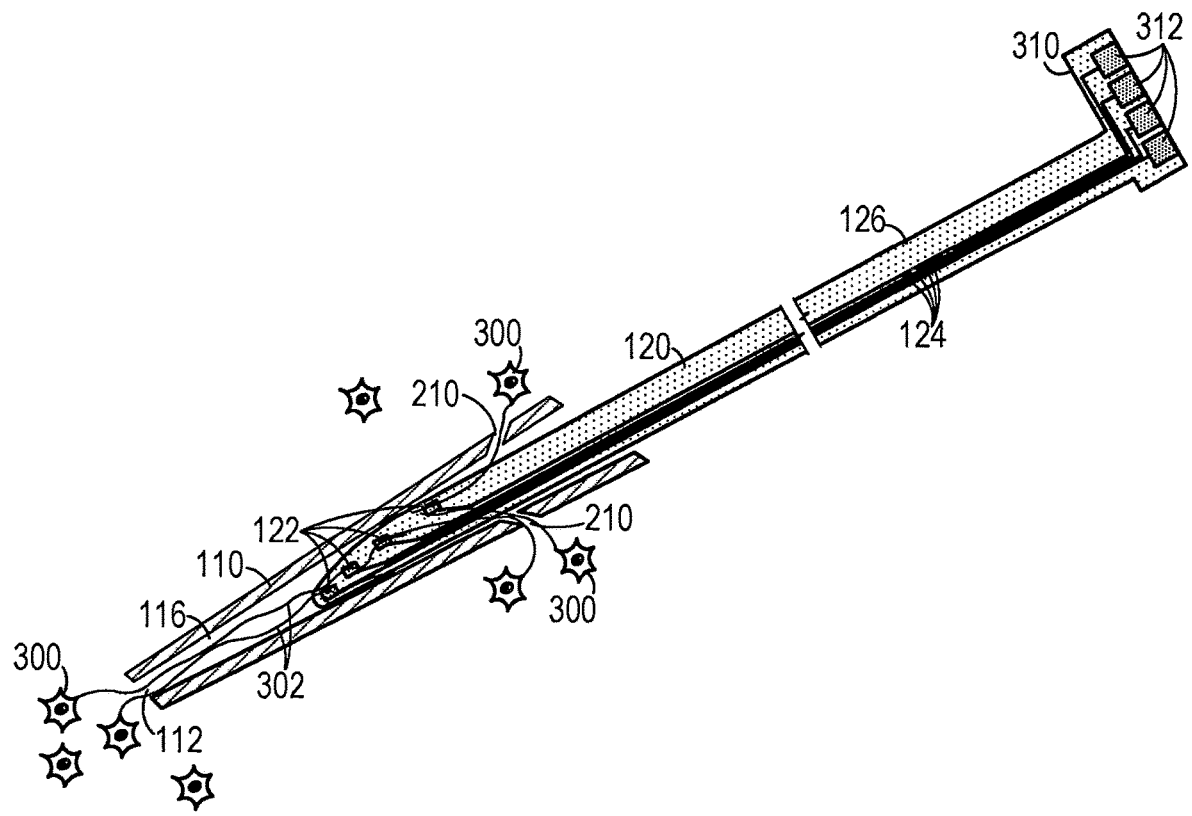
FIG. 3 is a schematic diagram of the embodiment shown in FIG. 2.

As shown in FIG. 3, one embodiment includes an elongated multi-channel electrode assembly 120 that terminates to a coupling surface 310 on which are exposed connection pads 312 for coupling the electrode to an external signal detection apparatus. While the wires 124 are embedded in the dielectric ribbon 126 or insulated with an applied resin, the recording sites 122 and the connection pads 312 are not insulated. The figure also shows neurites 302 extending from neurons 300 having grown in through passages 112 and 210 and in communication with the recording sites 122.

Figure 4A:
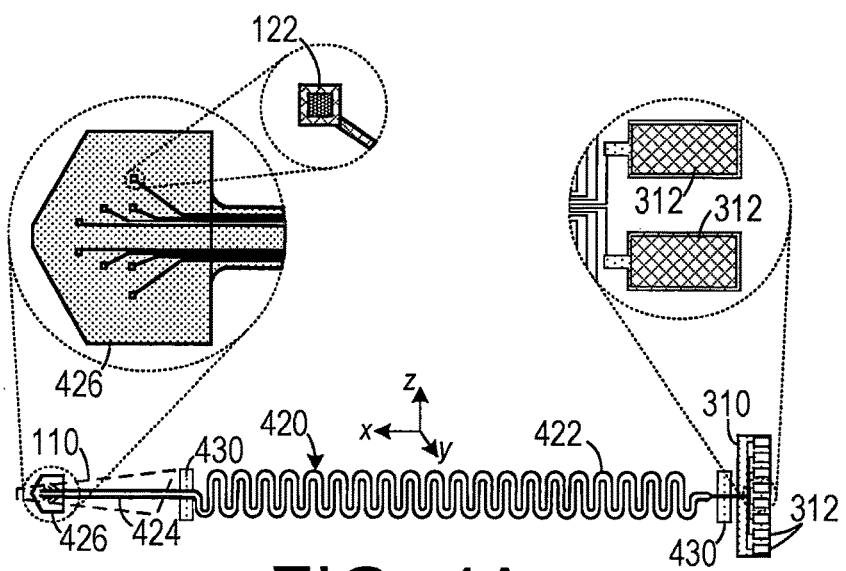
FIG. 4A is a schematic diagram of an embodiment of a multi-channel electrode assembly employing an undulating dielectric ribbon.
Figure 4B:
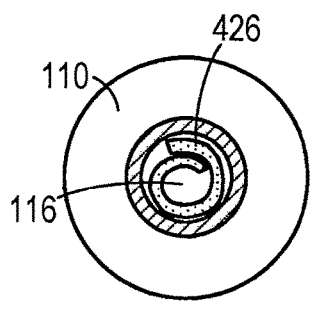
FIG. 4B is a narrow end view of a neurotrophic electrode employing the multi-channel electrode assembly shown in FIG. 4A.

An alternate multi-channel electrode assembly 420 is shown in FIG. 4A, in which the dielectric ribbon 420 includes a straight portion 424 and an undulated ribbon portion 422 that extends outside of the cone 110. The undulated ribbon portion 422 is flexible in three axes that are orthogonal to each other (e.g., the x, y & z axes). A manipulation tab 430 can be attached to the ribbon 422 on either end (or on both ends) to provide a surface for holding and manipulating the electrode assembly during implantation. The straight portion 424 terminates in an end tab 426 on which the recording sites 122 are disposed. As shown in FIG. 4B, the end tab 426 is rolled up inside of the cavity 116 defined by the cone 110.

Figure 5A:
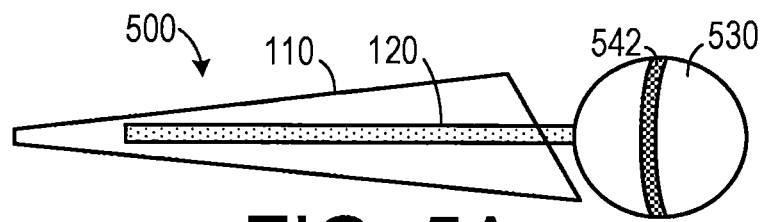
FIG. 5A is a schematic diagram of an embodiment that includes a data acquisition and transmission module.
Figure 5B:
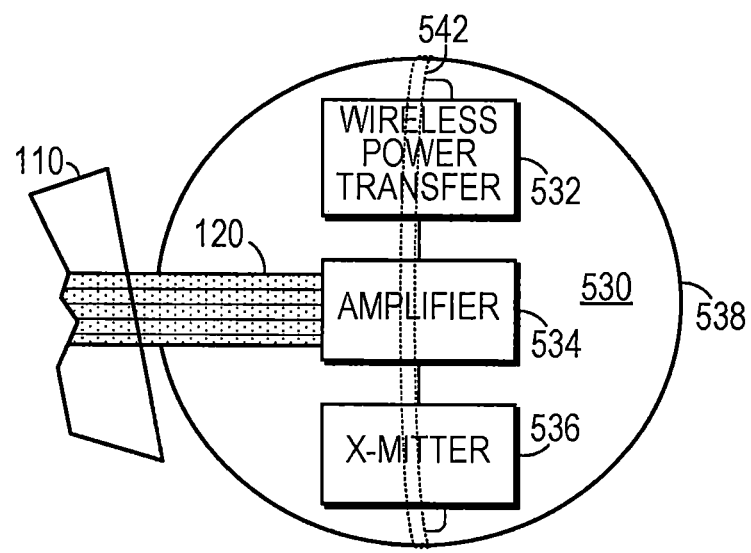
FIG. 5B is a schematic diagram of the embodiment shown in FIG. 5A, showing a detail of the data acquisition and transmission module.

As shown in FIGS. 5A and 5B, one embodiment can be adapted for remote sensing in which the electrode assembly 500 is not physically coupled to a device that is external from the body. Such an assembly 500 includes a data acquisition and transmission module 530 that is coupled to the multi-channel electrode assembly 120. The data acquisition and transmission module 530 includes a wireless power transfer device 532 that receives a wireless signal from a remote device and that generates electrical power in response thereto. An amplifier 534, which is in data communication with the multi-channel electrode assembly 120, receives electrical power from the wireless power transfer device 532. The amplifier 534 amplifies data from the multi-channel electrode assembly 120 and communicates amplified data to a transmitter 536. The transmitter 536, which is powered by the wireless power transfer device 532, generates a wireless signal corresponding to amplified data. A bio-compatible casing 538 (such as a glass or plastic casing) envelops the data acquisition and transmission module 530. The bio-compatible casing 538 may be spaced apart from the second end of the cone 110 to accommodate tissue growth into the space there-between.

Figure 6:
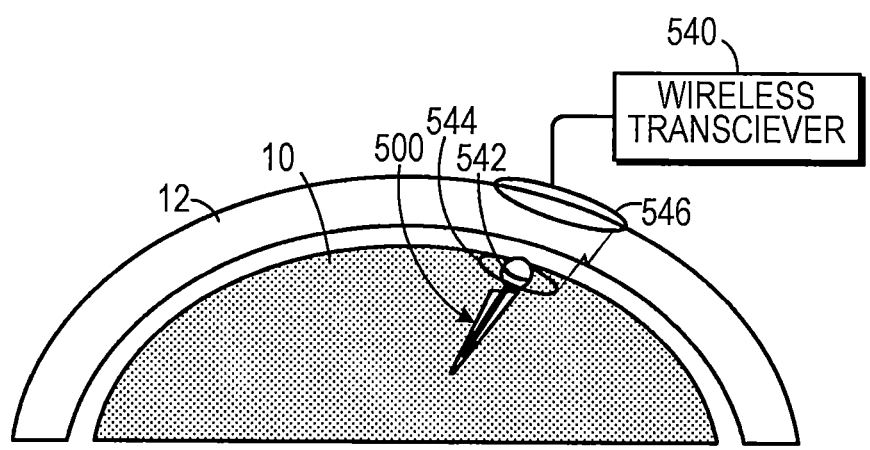
FIG. 6 is a schematic diagram demonstrating the embodiment of FIG. 5A implanted in a brain.

As shown in FIG. 6, after this embodiment is implanted in a brain 10, data acquired from the electrode system 500 can be acquired by a wireless transceiver device 540 without requiring wires passing through the skull 12. In this embodiment, a receiver coil 542 can be disposed about the periphery of the data acquisition and transmission module 530. A resonator coil 544 that has a resonant frequency that is common to a resonant frequency of the receiver coil 542 is disposed under the skull 12 about the data acquisition and transmission module 530. A transmitter coil 546, which has a resonant frequency in common with the resonator coil 544 and the receiver coil 542, is placed adjacent to the outside of the skull 12. Power is transferred to the electrode system 500 by applying a periodic signal to the transmitter coil 546, which causes it to resonate. This resonance induces a current in the resonator coil 544, which induces resonance therein. This resonance is inductively coupled to the receiver coil 542, which induces a current therein and causes power to be made available to the amplifier 534 and the transmitter 536. In collecting data, the process is essentially reversed: the transmitter 536 generates a signal onto which data from the amplifier 534 has been modulated. The signal is coupled to the receiver coil 542, inducing resonance that is inductively coupled to the resonator coil 544. This induces a resonating current in the resonator coil 544, which is inductively coupled to the transmitter coil 546. The signal induced in the transmitter coil 546 is detected and processed by the wireless transceiver device 540.

In other embodiments, the data acquisition and transmission module 530 could also include a memory module and a processor for more complex data processing. Also, the embodiment could be used for brain stimulation applications, in which the wireless transceiver 540 could be programmed to apply stimulating signals when certain neural potentials are sensed.

Figure 7:
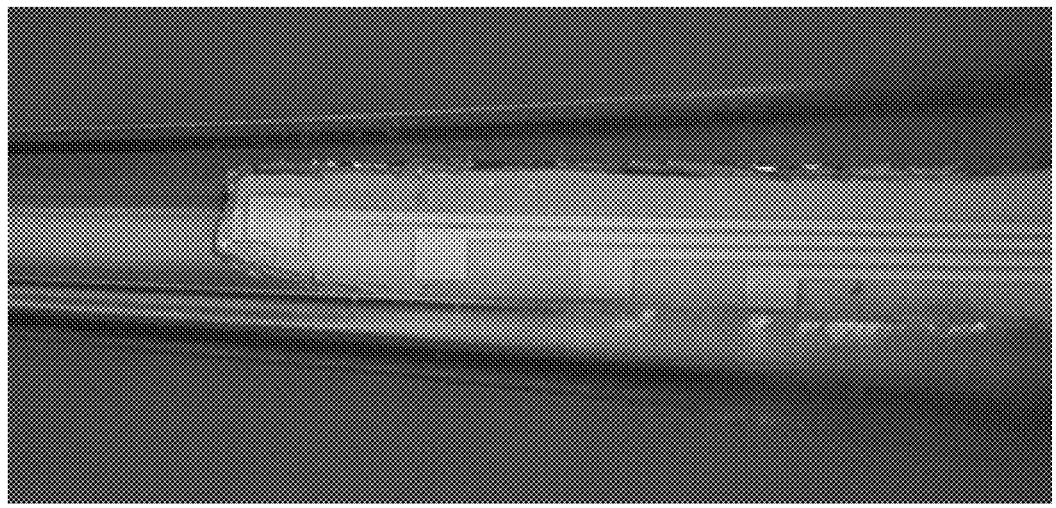
FIG. 7 is a photograph of a detail showing a detail of one experimental embodiment of a multi-channel electrode assembly.
Figure 8:
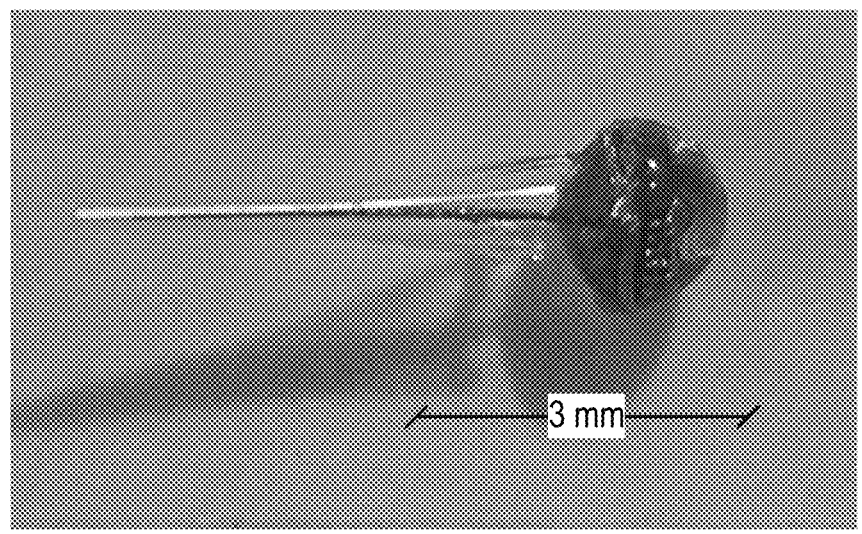
FIG. 8 is a photograph of an experimental embodiment of the device shown in FIG. 5A.

A photograph showing a detail of part of a multi-channel electrode assembly is shown in FIG. 7. A photograph of an embodiment employing a data acquisition and transmission module is shown in FIG. 8.

The above described embodiments, while including the preferred embodiment and the best mode of the invention known to the inventor at the time of filing, are given as illustrative examples only. It will be readily appreciated that many deviations may be made from the specific embodiments disclosed in this specification without departing from the spirit and scope of the invention. Accordingly, the scope of the invention is to be determined by the claims below rather than being limited to the specifically described embodiments above.

What is claimed is:

1. A neurotrophic electrode system, comprising:
    (a) a non-conductive cone that consists essentially of a material that is stable in a neural environment and that defines a cavity, the cavity opens to a small opening at a first end of the non-conductive cone and opens to a large opening at a second end of the non-conductive cone that is opposite the first end;
    (b) a multi-channel electrode assembly including at least two recording sites that are disposed within the cavity defined by the non-conductive cone, each recording site coupled to a wire that extends out of the large end of the non-conductive cone, each wire ending in a connection pad;
    (c) a dielectric ribbon that encases all of the wires but that exposes each recording site and that exposes each connection pad; and
    (d) a neurite-attracting substance disposed within the non-conductive cone, wherein the dielectric ribbon terminates in an end tab on which the recording sites are disposed and wherein the end tab is rolled up inside of the cavity defined by the non-conductive cone, and wherein at least one side opening is in communication with the cavity and is disposed between the large opening and the small opening.

2. The neurotrophic electrode system of claim 1, wherein the dielectric ribbon extends outside of the non-conductive cone to an undulated ribbon that is flexible in three axes that are orthogonal to each other.

3. The neurotrophic electrode system of claim 1, further comprising a data acquisition and transmission module coupled to the dielectric ribbon, the data acquisition and transmission module including:
    (a) a wireless power transfer device configured to receive a wireless signal and to generate electrical power in response thereto;
    (b) an amplifier that is in data communication with the multi-channel electrode assembly and that receives the electrical power from the wireless power transfer device, the amplifier configured to amplify data from the multi-channel electrode assembly;
    (c) a transmitter that receives the electrical power from the wireless power transfer device and in communication with the amplifier, the transmitter configured to generate a second wireless signal corresponding to the data amplified by the amplifier; and
    (d) a bio-compatible casing that envelops the wireless power transfer device, the amplifier, and the transmitter.

4. The neurotrophic electrode system of claim 3, wherein the bio-compatible casing is spaced apart from the second end of the non-conductive cone so as to accommodate tissue growth there-between.

5. The neurotrophic electrode system of claim 1, wherein the non-conductive cone comprises a material selected from a list consisting of: glass, quartz, silicon, and polyamide.

6. The neurotrophic electrode system of claim 1, wherein the dielectric ribbon comprises a material selected from a list consisting of: polyamide, polytetrafluoroethylene, and poly (p-xylylene) polymer.

7. The neurotrophic electrode system of claim 1, wherein the neurite-attracting substance comprises a substance selected from a list consisting of: neural growth factors, nerve segments, endothelium, stem cells, and combinations thereof.

8. The neurotrophic electrode system of claim 1, wherein each of the wires comprise a selected one of platinum or gold.

9. A neural electrode system, comprising:
    (a) a non-conductive cone that consists essentially of a material that is stable in a neural environment and that defines a cavity, the cavity opens to a small opening at a first end of the non-conductive cone and to a large opening at a second end of the non-conductive cone that is opposite the first end, the non-conductive cone defining at least one side opening in communication with the cavity in which the side opening is disposed between the large opening and the small opening;
    (b) a multi-channel electrode assembly including at least two recording sites that are disposed within the cavity defined by the non-conductive cone, each recording site coupled to a wire that extends out of the large end of the non-conductive cone, each wire ending in a connection pad;
    (c) a dielectric ribbon that encases all of the wires but that exposes each recording site and that exposes each connection pad; and
    (d) a neurite-attracting substance disposed within the non-conductive cone, wherein the dielectric ribbon terminates in an end tab on which the recording sites are disposed and wherein the end tab is rolled up inside of the cavity defined by the non-conductive cone.

10. The neural electrode system of claim 9, wherein the dielectric ribbon extends outside of the non-conductive cone to an undulated ribbon that is flexible in three axes that are orthogonal to each other.

11. The neural electrode system of claim 9, further comprising a data acquisition and transmission module coupled to the dielectric ribbon, the data acquisition and transmission module including:
    (a) a wireless power transfer device configured to receive a wireless signal and to generate electrical power in response thereto;
    (b) an amplifier that is in data communication with the multi-channel electrode assembly and that receives the electrical power from the wireless power transfer device, the amplifier configured to amplify data from the multi-channel electrode assembly;
    (c) a transmitter that receives the electrical power from the wireless power transfer device and in communication with the amplifier, the transmitter configured to generate a second wireless signal corresponding to the data amplified by the amplifier; and
    (d) a bio-compatible casing that envelops the wireless power transfer device, the amplifier, and the transmitter.

12. The neural electrode system of claim 9, wherein the non-conductive cone comprises a material selected from a list consisting of: glass, quartz, silicon, and polyamide.

13. The neural electrode system of claim 9, wherein the dielectric ribbon comprises a material selected from a list consisting of: polyamide, polytetrafluoroethylene, and poly(p-xylylene) polymer.

14. The neural electrode system of claim 9, wherein the neurite-attracting substance comprises a substance selected from a list consisting of: neural growth factors, nerve segments, endothelium, stem cells, and combinations thereof.

15. The neural electrode system of claim 9, wherein each of the wires comprise a selected one of platinum or gold.

16. A neural electrode system, comprising:
   (a) a non-conductive cone that consists essentially of a material that is stable in a neural environment and that defines a cavity, the cavity opens to a small opening at a first end of the non-conductive cone and to a large opening at a second end of the non-conductive cone that is opposite the first end, the non-conductive cone defining at least one side opening in communication with the cavity in which the side opening is disposed between the large opening and the small opening;
   (b) a multi-channel electrode assembly including at least two recording sites that are disposed within the cavity defined by the non-conductive cone, each recording site coupled to a wire that extends out of the large end of the non-conductive cone, each wire ending in a connection pad;
   (c) a dielectric ribbon that encases all of the wires but that exposes each recording site and that exposes each connection pad; and
   (d) a neurite-attracting substance disposed within the non-conductive cone,
   wherein the dielectric ribbon terminates in an end tab on which the recording sites are disposed and wherein the end tab is rolled up inside of the cavity defined by the non-conductive cone, and wherein each of the wires comprise a selected one of platinum or gold.

17. The neural electrode system of claim 16, wherein the dielectric ribbon extends outside of the non-conductive cone to an undulated ribbon that is flexible in three axes that are orthogonal to each other.

18. The neural electrode system of claim 16, filthier comprising a data acquisition and transmission module coupled to the dielectric ribbon, the data acquisition and transmission module including:
   (a) a wireless power transfer device configured to receive a wireless signal and to generate electrical power in response thereto;
   (b) an amplifier that is in data communication with the multi-channel electrode assembly and that receives the electrical power from the wireless power transfer device, the amplifier configured to amplify data from the multi-channel electrode assembly;
   (c) a transmitter that receives the electrical power from the wireless power transfer device and in communication with the amplifier, the transmitter configured to generate a second wireless signal corresponding to the data amplified by the amplifier; and
   (d) a bio-compatible casing that envelops the wireless power transfer device, the amplifier, and the transmitter.

19. The neural electrode system of claim 16, wherein the non-conductive cone comprises a material selected from a list consisting of: glass, quartz, silicon, and polyamide and wherein the dielectric ribbon comprises a material selected from a list consisting of: polyamide, polytetrafluoroethylene, and poly(p-xylylene) polymer.

* * * * *